United States Patent [19]
McEwen et al.

[11] Patent Number: 5,271,384
[45] Date of Patent: Dec. 21, 1993

[54] POWERED SURGICAL RETRACTOR

[76] Inventors: James A. McEwen, 10551 Bamberton Drive, Richmond, B.C., Canada, V7A 1K6; Geoffrey F. Auchinleck, #5 - 1182 West 7th Ave., Vancouver, B.C., Canada, V6H 1B4; Carlo R. Bussani, 3884 West 15th Avenue, Vancouver, B.C., Canada, V6R 2Z9; Mark N. Dance, 1461 Walnut St., Vancouver, B.C., Canada, V6J 3R2

[21] Appl. No.: 825,655

[22] Filed: Jan. 23, 1992

Related U.S. Application Data

[63] Continuation of Ser. No. 762,639, Sep. 18, 1991, Pat. No. 5,201,325, which is a continuation-in-part of Ser. No. 401,824, Sep. 1, 1989, abandoned.

[51] Int. Cl.$^5$ .............................................. A61B 17/02
[52] U.S. Cl. ...................................... 128/20; 248/904; 901/22; 901/41
[58] Field of Search ............... 128/17, 18, 19, 20; 248/904, 404, 295.1, 225.31, 669; 269/20, 24, 27; 318/568.13; 606/53; 901/22, 41

[56] References Cited

U.S. PATENT DOCUMENTS

| H297 | 7/1987 | Schultz | 901/41 X |
|---|---|---|---|
| 2,124,006 | 7/1938 | Parker | 248/904 X |
| 4,229,136 | 10/1980 | Panissidi | 901/22 |
| 4,971,037 | 11/1990 | Pelta | 128/20 |
| 5,078,140 | 1/1992 | Kwoh | 901/41 X |
| 5,154,717 | 10/1992 | Matsen, III et al. | 606/53 |

OTHER PUBLICATIONS

Aesculap General Surgical Catalogue, 3-page reprint, USA, 1983.

*Primary Examiner*—Peter A. Aschenbrenner
*Attorney, Agent, or Firm*—Klarquist Sparkman Campbell Leigh & Whinston

[57] ABSTRACT

Apparatus useful in surgery for holding surgical instruments such as retractor blades in a number of different positions required by a surgeon for the performance of a surgical procedure, including an actuation means responsive to a control signal, a signal generating means which enables an operator to generate the control signal and which transmits the control signal to the actuation means, for causing the actuation means to move the surgical instrument.

17 Claims, 7 Drawing Sheets

POWERED SURGICAL RETRACTOR

This application is a continuation of U.S. patent application Ser. No. 07/762,639, filed Sep. 18, 1991, now U.S. No. 5,201,325, which is a continuation-in-part of U.S. patent application Ser. No. 07/401,824 filed Sep. 1, 1989, now abandoned.

FIELD OF THE INVENTION

This invention pertains to an apparatus for positioning surgical instruments such as, but not limited to, retractor blades in a number of different orientations required by a surgeon for the performance of a surgical procedure, and to a means which enable an operator to cause the apparatus to apply a force to the surgical instrument in order to move it in a desired direction. In particular, this invention pertains to apparatus comprising a plurality of positioning members interconnecting a means for holding surgical instruments to a supporting point, each member including positionable joints which may be locked in a selected position, actuation means responsive to a control signal, and signal generating means which enables an operator to generate a control signal and which transmits the control signal to the actuation means for causing the actuation means to move the surgical instrument.

BACKGROUND OF THE INVENTION

Many surgical procedures require that surgical instruments such as retractor blades be positioned in a number of different positions in order to perform a certain surgical task. It is desirable that the operating surgeon or surgical assistant be able to directly move the retractor blade into various positions and configurations that may be required. It is also desirable that any surgical retractor that may be used to achieve such positions and configurations not obstruct the surgical site, and be able to avoid any obstacles that may exist around the surgical site, such as medical imaging systems, operating room lights, instrument trays, or other apparatus. The surgical retractor should also be stable, easy to control and re-position precisely, require no attention between changes in position in order to free the surgeon's hands to perform other tasks, and be sufficiently strong and rigid to hold a set position reliably, yet be light enough to allow the surgeon to easily achieve a desired position and orientation of the retractor blade. It is also desirable, in many applications, that the surgical retractor provide a means to apply a force to the retractor blade in a desired direction under control of the surgeon through the generation of a control signal to adjust the position of the surgical instrument. This is particularly true of situations in which surgical retraction in a vertical direction is desired. Vertical retraction, which is required in mammoplasty surgery for example, is very difficult to achieve with hand-held surgical instruments.

Various methods for positioning and holding surgical instruments such as retractor blades are known in the prior art. One common method for positioning a retractor blade is to have a surgical assistant hold the retractor blade in a desired position, and change the position when and as requested by the operating surgeon. This task is fatiguing for the surgical assistant, and may not provide sufficiently precise and rigid support for the retractor blade in some surgical procedures.

In addition to the method for positioning described above, apparatus for positioning retractor blades exists in the art. One typical retractor blade positioning apparatus consists of a vertical mounting frame fastened to the operating room table, to which are fastened at discrete but adjustable positions different retractor blades to provide an upward pulling force on tissues or organs (e.g. Aesculap BT710 Fixation Device and Aesculap BT711-BT715 Rochard abdominal retractor blades, Aescualp Instruments Corp, Burlingame, Calif. U.S.A.). Ropes, weights, and pulley systems are also used in conjunction with the vertical frame to provide a continuously adjustable positioning system. Similar abdominal retraction techniques utilize a horizontal frame laid on the patient's body to which are fastened at discrete but adjustable positions different retractor blades to provide a lateral pulling force on tissues or organs (e.g. Aesculap BV662 frame and Aesculap BV668 blades). These types of surgical retractors are difficult to set up and take down, clumsy to adjust, and often obstruct the surgical site. Furthermore, adjusting such apparatus to achieve a new position may require the assistance of a non-sterile person, in that operating room fixtures and support stands that may require re-positioning are not considered sterile, hence cannot be touched by a surgeon. This may preclude optimal positioning of the retractor blades or tissue, as the surgeon may no longer have direct control over the final position of the retractor blade. These types of retractor blade positioning systems are limited in their range of adjustment, versatility of orientation, precision of positioning, and rigidity of support.

Additional specialized positioning devices for holding retractor blades are known in the art. The Elmed Company of Addison Illinois manufactures a multi-jointed mechanism, the "Elmed Retract-Robot", catalog number 15088-00 single arm instrument, which can be locked in a wide range of positions with a thumb-screw arrangement. However this device is not suitable for a wide range of surgical procedures due to its inconsistent locking strength, limited range of motion, inability to unlock joints separately for re-positioning, time-consuming and tedious adjustment of the thumb screw, potential for obstruction of the surgical site, and solid steel construction which is not x-ray translucent. It is conceivable that several such devices could be connected together to create a larger structure with an increased range of motion, but such a structure would be very difficult to re-position, in that each device in the structure would have to be unlocked, positioned and locked individually each time a new position is required. In addition, it is unlikely that several such devices connected together would offer sufficient strength for the intended application. Finally, this device offers no means for a user to generate a control signal to adjust the position of the surgical instrument, and no means for applying a force to move the surgical instrument.

Also known in the art is a retractor blade holding device, widely known by surgeons throughout the world as a "Greenberg" brain retractor. This surgical retractor consists of a plurality of ball and socket joints, threaded upon a length of cable. This cable may be tightened with a lever mechanism to increase the friction between each ball and socket joint. The Greenberg brain retractor is not suitable for all surgical procedures due to its typically small size. In addition, the strength of the ball and socket joints when fully locked is insufficient to support the loads typically expected when positioning retractor blades in many surgical procedures. The device is not x-ray translucent, nor is it capable of allowing the user to generate a control signal to adjust the position of the device.

SUMMARY OF THE INVENTION

The present invention provides apparatus for holding a surgical instrument in a number of different positions required by a surgeon for the performance of a surgical procedure, a grasping means for surgical instruments, an actuation means for changing the position of the surgical instrument in response to a control signal, signal generating means which enables an operator to generate the control signal and which transmits the control signal to the actuation means to move the surgical instrument. The present invention further comprises one or more positioning members interconnecting a supporting point to the grasping means, each positioning member having positionable joints attached to attaching means for connecting each positioning member to other such members, or to the grasping means or to the supporting point. Each positioning member also includes a locking means for locking the positionable joints in a selected position, an actuating means for locking and unlocking the locking means in response to a control signal, and a control signal generating means by which an operator can generate control signals for locking and unlocking the positionable joints.

Other objects of the present invention include: providing a control signal generating means for locking and unlocking the joints of the apparatus which is attached to the surgical instrument such that an operator must be in contact with the apparatus to unlock it, and providing a apparatus that may be largely constructed out of X-ray translucent materials so that the positioning members will minimally interfere with medical X-ray images taken of the body while the apparatus is being used.

DETAILED DESCRIPTION OF THE PREFERRED EMBODIMENT

Figure 1:
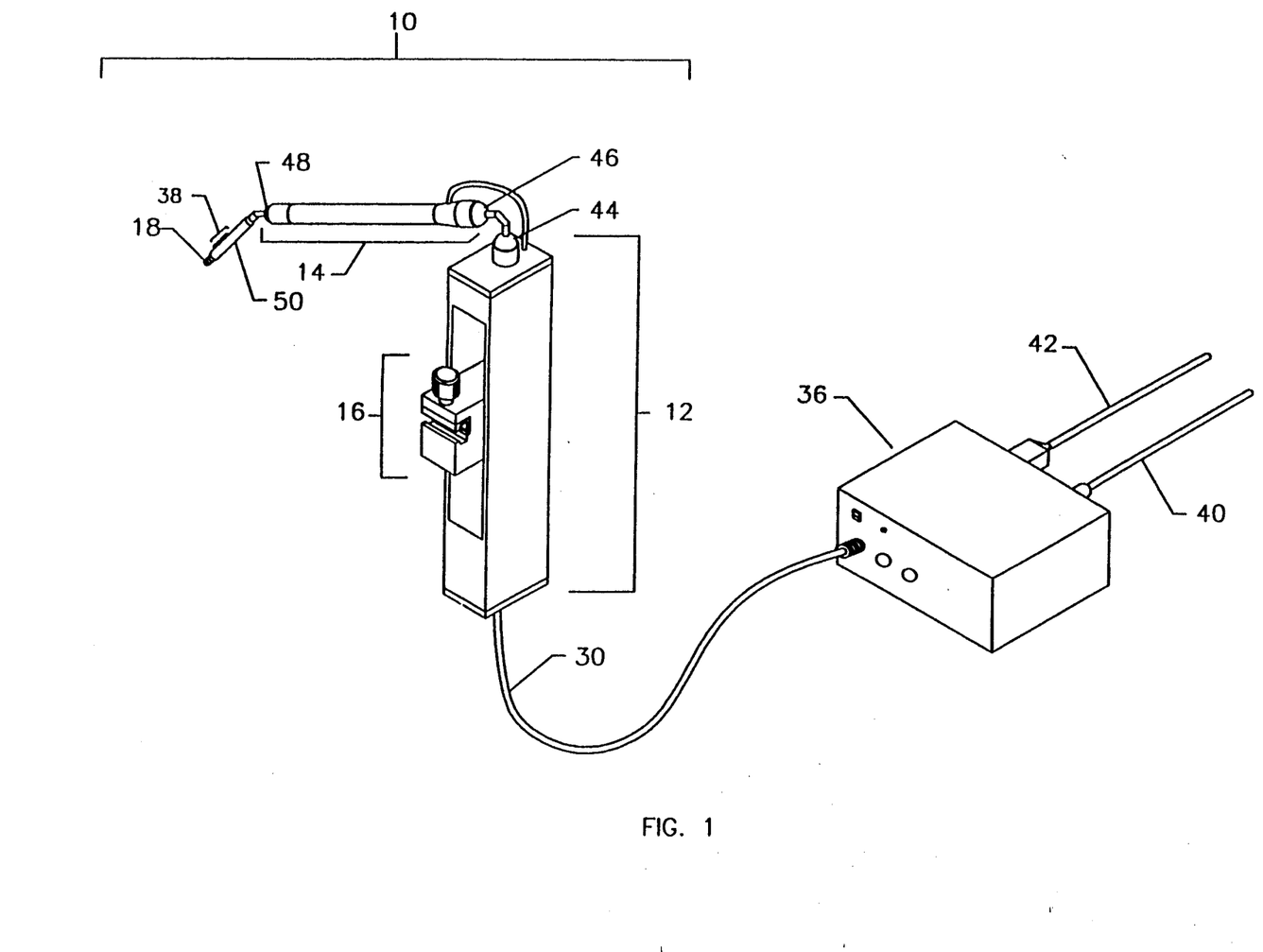
FIG. 1 is a pictorial illustration of the preferred embodiment of a surgical retractor system for assisting in the performance of surgical procedures.

FIG. 1 shows a preferred embodiment of the present invention, configured as a surgical retraction system. The retraction system comprises surgical retractor 10, for positioning surgical instruments with respect to the operating table, and control box 36, for controlling the response of the retraction system.

Surgical retractor 10 includes three connected members, elevating member 12 distal member 14 and switch housing 50. Elevating member 12 includes table mounting means 16 for attaching surgical retractor 10 to an operating table side rail (not shown) and mechanisms for elevating surgical retractor 10 in the vertical plane with respect to table mounting means 16 by applying a known force. Distal member 14 is moveably connected to elevating member 12 by lockable ball joints 44 and 46. In a similar manner, switch housing 50 is moveably connected to distal member 14 by lockable distal ball joint 48. Located in switch housing 50 are switches 38 for specifying a desired response of the retraction system such as elevation of surgical retractor 10 or lock or unlock ball joints 44, 46 and 48. Also located in switch housing 50 is connector 18, for attachment of surgical retractor blades or instruments (not shown).

In the configuration shown, surgical retractor 10, when attached to an operating table, advantageously provides positioning of surgical retractors or instruments in a wide continuum of locations and orientations with respect to the operating table. Further, when retractor 10 is removed from the operating table, the configuration of surgical retractor 10 permits distal member 14 to be positioned parallel to elevating member 12 in a manner convenient for storage.

In operation control box 36 is provided with pressurized gas through pneumatic hose 40 and electrical power through electrical cord 42. In the preferred embodiment, pneumatic hose 40 is coaxial to permit the return of exhausted gas from surgical retractor 10 in a manner which reduces contamination of the surgical site. Control box 36 is detachably connected to surgical retractor 10 by cable 30 which contains pneumatic tubes and electrical lines for providing conditioned electrical and pneumatic communication between control box 36 and surgical retractor 10. Control box 36 includes electrical and pneumatic control devices for receiving electrical signals from surgical retractor 10 and providing or receiving pressurized gas to or from surgical retractor 10 in response to the electrical signals.

Referring now to FIG. 2a through 2e, specific construction of the preferred embodiment of surgical retractor 10 is described.

Figure 2A:
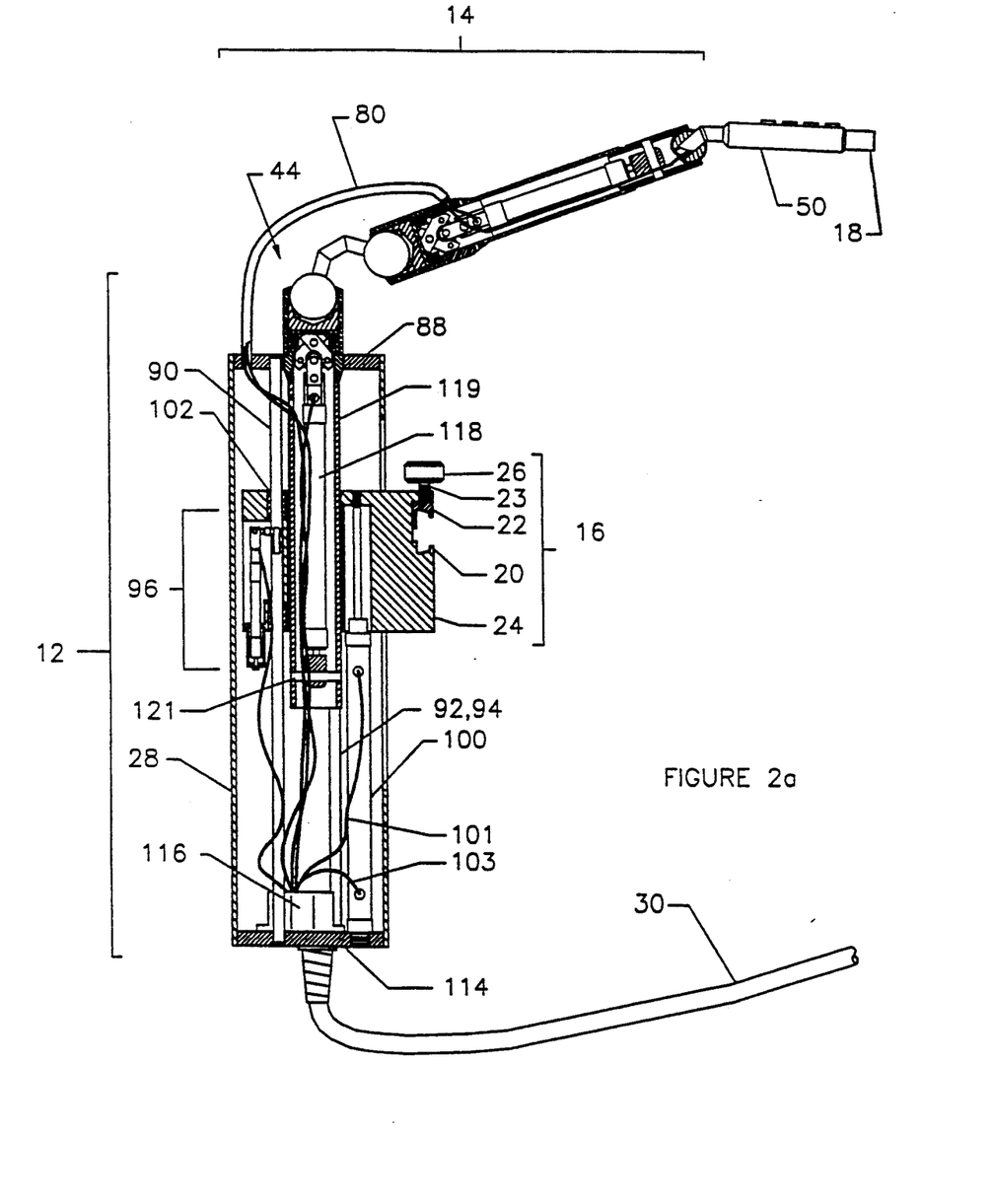
FIG. 2a shows a cross section of the preferred embodiment.

As shown in FIG. 2a, table mounting means 16 provides means for connecting surgical retractor 10 to the side rail of an operating room table and consists of two jaws, fixed lower jaw 20 attached to block 24 and movable upper jaw 22 which translates with threaded shaft 23 connected to knurled knob 26. Rotation of knob 26 causes threaded shaft 23 to travel through block 24, forcing movable jaw 22 towards fixed lower jaw 20, thereby permitting the rail of an operating table to be rigidly clamped between upper jaw 22 and lower jaw 20.

Construction of elevating member 12 permits vertical motion of distal module 14 and connected switch housing 50 with respect to block 24. Passing through block 24 are three equally spaced guide rods 90, 92, and 94 which are constrained to vertical translation with respect to block 24 by six linear bearings 102 mounted in block 24. Guide rods 90, 92 and 94 are coupled by top end plate 88 and bottom end plate 114 such that the guide rods and end plates form a carriage which translates as a unit with respect to block 24. Distal member 14 and connected switch housing 50 are attached to top end plate 88 through ball joint 44, and associated ball joint restraint and locking mechanisms which will be later described, so that distal member 14 and connected switch housing 50 may be caused to move vertically relative to block 24 when top end plate 88 is moved.

Controlled motion of top end plate 88 relative to block 24 is provided by pneumatic cylinder 100 and pneumatic control means 116. Pneumatic cylinder 100 is attached between block 24 and bottom end plate 114 and receives and discharges gas through tubes 101 and 103 to pneumatic control means 116. Pneumatic control means 116, preferably consisting of electrically controllable valves, receives a supply of pressurized gas from the control unit through cable 30 and distributes this gas to the pneumatic actuators situated throughout the surgical retractor. Control of the gas pressure within cylinder 100 causes a force to be applied between bottom end plate 114 and block 24. When the generated force is greater than external forces acting on the surgical retractor, such as the weight of distal member 14 or a force applied by a surgical instrument through connector 18 attached to switch housing 50, motion of bottom end plate 114 relative to block 24 is achieved. By virtue of the connective relationship of bottom end plate 114, top end plate 88 and switch housing 50, application of a vertical force between surgical instruments attached to switch housing 50 and an operating table to which block 24 is attached can be controllably achieved.

Elevating member 12 also comprises cowling 28 which is fastened to top end plate 88 and bottom end plate 114 and moves with these end plates with respect to block 24. In order to provide unrestricted vertical motion, cowling 28 provides an opening through which block 24 passes permitting attachment of surgical retractor 10 to an operating table. In practice, a flexible sleeve would additionally be placed over cowling 28 so as to close the opening in cowling 28 to passage of fluids or contaminants yet permit unrestrained motion of block 24 with respect to cowling 28.

Figure 2B:
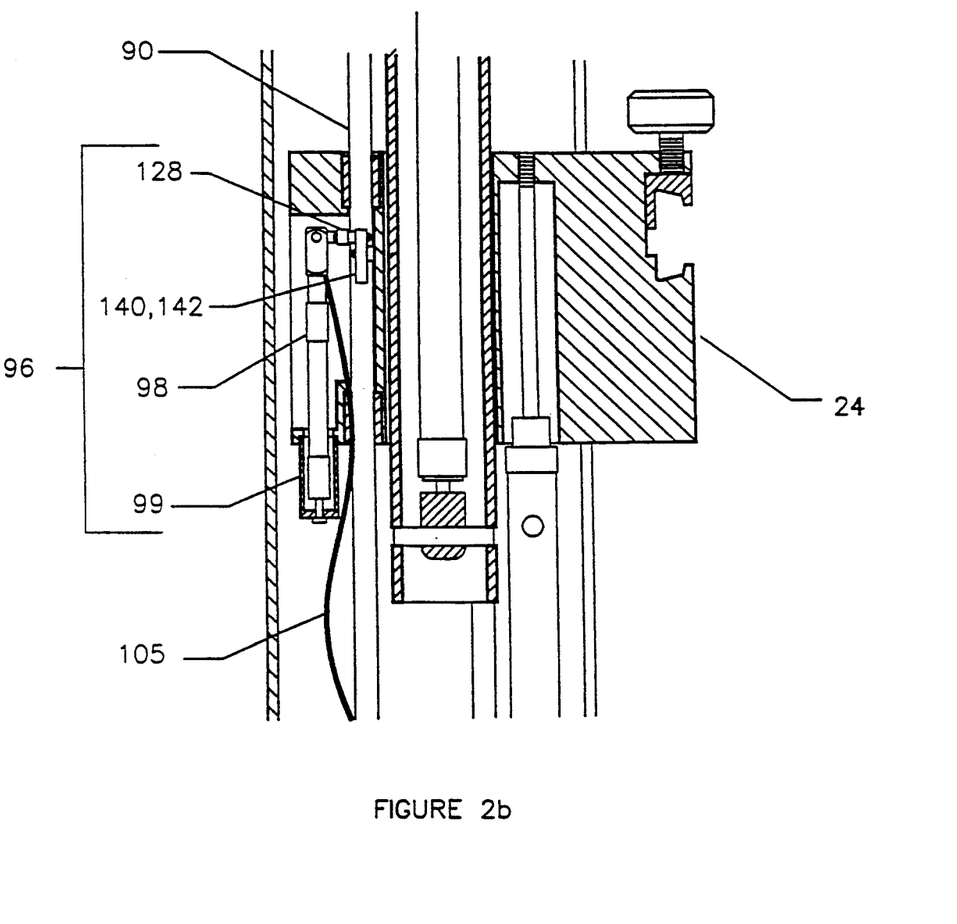
FIG. 2b shows an enlarged cross section of the stationary mounting clamp and the elevator brake of the preferred embodiment.
Figure 2C:
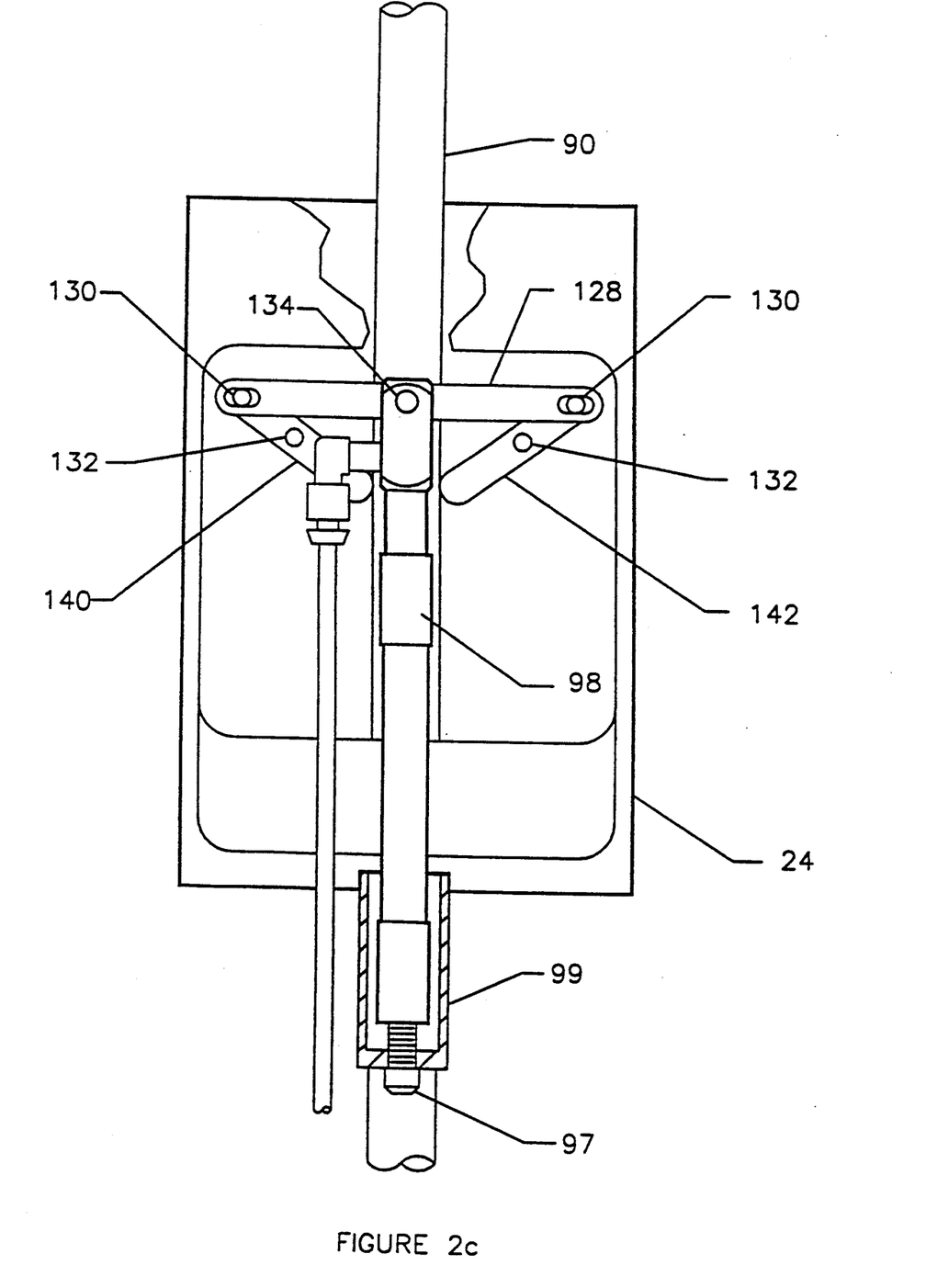
FIG. 2c shows an alternate enlarged view of the elevator brake of the preferred embodiment.

When vertical translation of ball joint 44 and distal member 14 relative to block 24 is not desired, braking means 96 is actuated to prevent such motion. An enlarged side view of braking means 96 is shown in FIG. 2b while an enlarged end view is shown in FIG. 2c. In FIG. 2c A portion of block 24 have been removed for clarity to show the orientation of guide rod 90 behind.

Braking means 96 consists of a pneumatic brake actuator 98 such as a Rubbertutator TM (Bridgestone Corp., Tokyo, Japan), brake actuator frame 99, tie bar 128 and brake levers 140 and 142. Braking means 96 is fixed relative to block 24 by two pivot pins 132 which pass through brake levers 140 and 142 and into block 24. Pivot pins 132 locate brake levers 140 and 142 equally about guide rod 90 and in proximity to guide rod 90 such that the ends of brake levers 140 and 142 may be brought into contact with guide rod 90 when levers 140 and 142 are rotated. Tie bar 128 is connected to brake levers 140 and 142 by two sliding pins 130, which permit rotation and restricted translation of brake levers 140 and 142 relative to tie bar 128. One end of pneumatic brake actuator 98 is connected to tie bar 128 by actuator pin 134 while the other end of brake actuator 98 is fixed to brake actuator frame 99 by bolt 97. Brake actuator frame 99 is, in turn, fixedly connected to block 24. In practice, all pinned joints created in braking means 96 include fasteners, such as circlips which are well known for this application, to prevent decoupling of the members at the pinned joints.

In use, pressurized gas is supplied to pneumatic brake actuator 98 through brake line 105 causing pneumatic brake actuator 98 to contract and pull tie bar 128 towards brake actuator frame 99 and downwards with respect to block 24. The contraction force of pneumatic brake actuator 98 is transferred to brake levers 140 and 142 by tie bar 128. Brake levers 140 and 142 rotate about pivot pins 132 and bear against guide rod 90 creating a high force between guide rod 90 and brake levers 140 and 142. The frictional component created by the force applied to guide rod 90 prevents motion of guide rod 90 with respect to brake levers 140 and 142, and with therefore respect to block 24 to which levers 140 and 142 are attached. Restricting motion of guide rod 90 in this manner prevents vertical translation of top end plate 88 and attached ball joint 44 with respect to block 24. Conversely, exhausting pneumatic brake actuator 98 removes the force applied to guide rod 90 by brake levers 140 and 142 and permits vertical translation of ball joint 44 with respect to block 24.

In the preferred embodiment two types of ball joint mechanisms are used. The first type of ball joint mechanism is shown in enlarged sectional view in FIG. 2d and is employed in ball joints 44 and 46 attached to top end plate 88 to connect elevating member 12 and distal member 14. As the mechanisms used by ball joints 44 and 46 are similar in construction and operation, only ball joint 46 will be described and should be considered generally indicative of both ball joints. Alterations in construction and operation between the joints will be noted where appropriate.

Figure 2D:
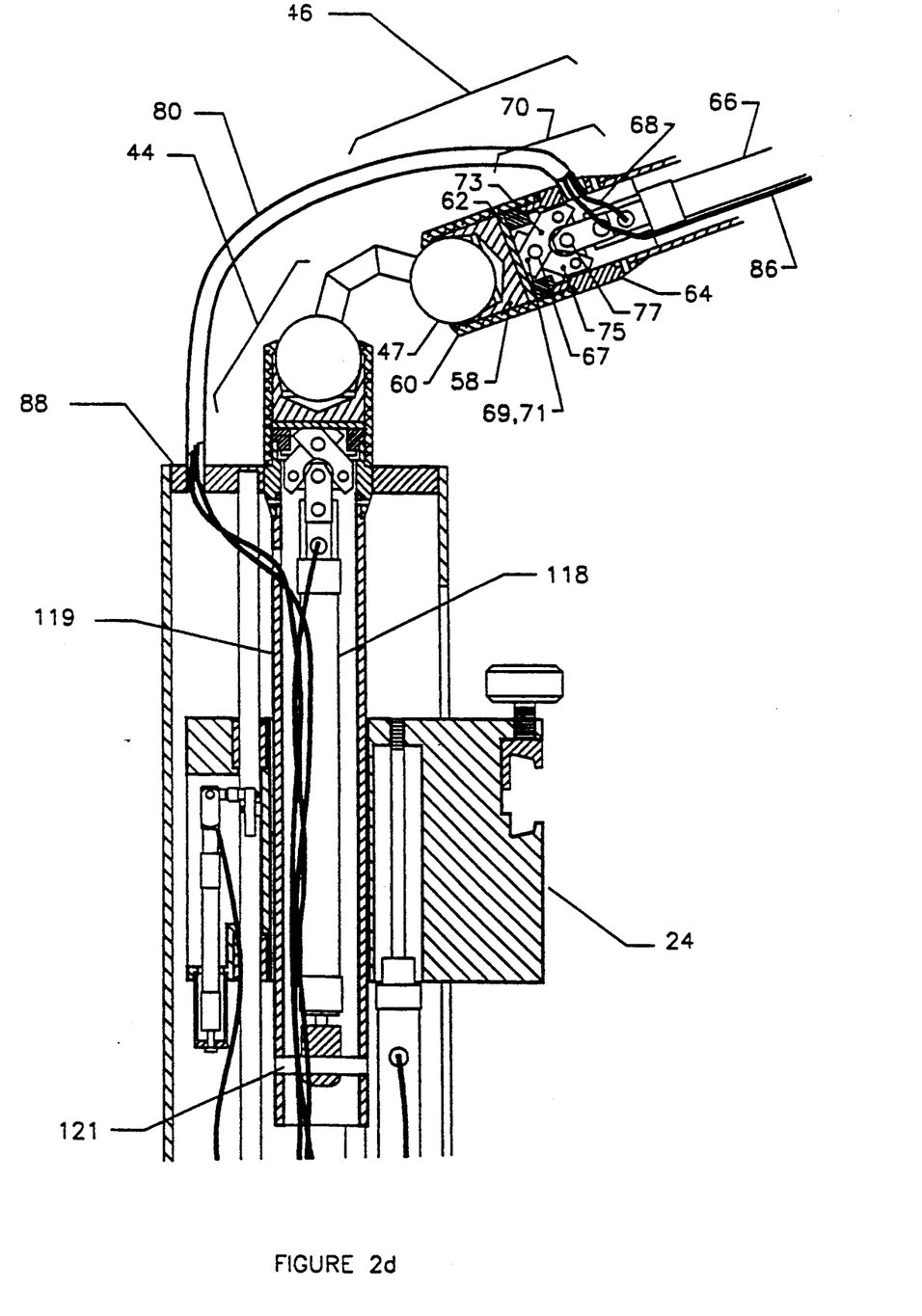
FIG. 2d shows an enlarged cross section of the connection between the distal member and the elevating member of the preferred embodiment.

Ball joint 44 consists of ball 47, cup 58, threaded cap 60, lever mechanism 70, separator plate 62, threaded module insert 64, distal pneumatic actuator 66 such as a Rubbertuator TM (Bridgestone Corp., Tokyo, Japan), and pneumatic hose 68. In the relaxed state, ball 47 is held captive but is free to rotate between cup 58 and threaded cap 60, both having appropriately contoured surfaces for improving their contact with ball 47, and hard finishes to provide a hard durable contact surface. Cup 58, and separator plate 62 are held together in close contact within threaded cap 60 by threaded insert 64. Lever mechanism 70 is contained within threaded insert 64.

In ball joint 46, one end of distal pneumatic actuator 66, is connected to lever mechanism 70 and passes through threaded insert 64. The opposite end of pneumatic actuator 66 is used to lock distal ball joint 48 (not shown) and will be described later. In ball joint 44 one end of proximal pneumatic actuator 118 is connected to lever mechanism 79, similar to lever mechanism 70, while the opposite is fixed to structural member 119 by clevis pin 121. Structural member 119 is fixedly attached to and extends downward from ball joint 44 and transmits a contraction force to ball joint 44 when proximal pneumatic actuator 118 is inflated. Structural member 119 moves with upper end plate 88 and passes through block 24 so as not to restrict vertical translation of upper end plate 88 with respect to block 24.

Pneumatic tube 68, and companion electrical wires 86, are conducted around ball joints 44 and 46 by external cable conduit 80 and pass through a small opening in threaded insert 64. Pneumatic tube 68 conducts pressurized gas into and exhaust gas from distal pneumatic actuator 66 from pneumatic control means 116 previously described (not shown). External cable conduit 80 also serves to limit rotation of distal member 14 to less than 360 degrees around the cylindrical axis of elevating member 12.

Lever mechanism 70 is a symmetrical scissor-action device, comprising levers 73 and 75 pinned together at hinge 67, which causes contact shoulders 69 and 71 of levers 73 and 75 to be pushed against separator plate 62 when distal pneumatic actuator 66 contracts. When activated, pneumatic hose 68 supplies pressurized gas to distal pneumatic actuator 66 which pulls on pin 77 of lever mechanism 70 and extends contact shoulders 69 and 71. By virtue of the moment arms employed by lever mechanism 70, the contraction force supplied by distal pneumatic actuator 66 is amplified and applied to separator plate 62. This amplified force is, in turn, exerted against cup 58 to create a high force to compress ball 47 between cup 58 and cap 60, thereby increasing the friction force between ball 47, cup 58 and cap 60, and locking ball 47 in position. The activating force applied to lever mechanism 70 by the pneumatic actuator 66 is proportional to the pressure of the pressurized gas supply. Advantageously in the preferred embodiment, the output force applied to the separator plate 62 by the lever mechanism 70 is an amplified force approximately four times the activating force applied by distal pneumatic actuator 66.

Figure 2E:
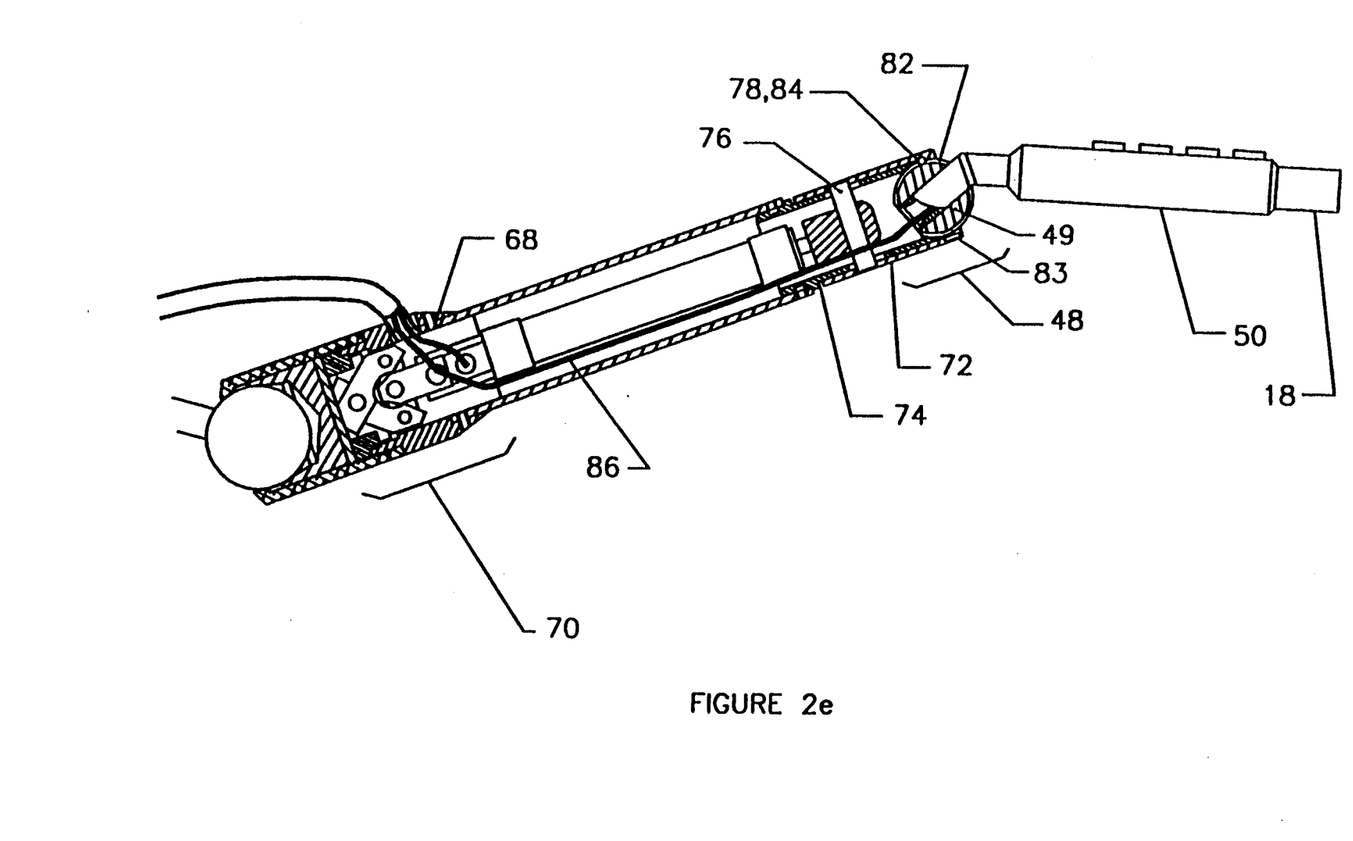
FIG. 2e shows an enlarged cross section of the distal member of the preferred embodiment.

The second type of ball joint mechanism is employed in distal ball joint 48 located at the distal end of distal member 14, as shown in FIG. 2e. Distal ball joint 48 consists of ball 49, cap 72, insert 74, clevis pin 76, bearing ball 78, and distal pneumatic actuator 66. In the relaxed state ball 49, is held captive but is free to rotate between cap 72, and insert 74, both having appropriately contoured surfaces for improving their contact with ball 49, and hard finishes to provide a hard durable contact surface. Ball 49, cap 70, and insert 74 are held in close contact and connected to distal pneumatic actuator 66 by clevis pin 76.

When activated, pneumatic hose 68 supplies pressurized gas to distal pneumatic actuator 66 which pulls on clevis pin 76 and hence cap 72 to create a high force which compresses ball 49 between cap 72 and insert 74, thereby increasing the friction force between ball 49, cap 72 and insert 74, and locking ball 49 in position. The activating force applied to cap 72 by the pneumatic actuator 66 is proportional to the pressure of the pressurized gas supply. Locking distal ball joint 48 through pressurization of distal pneumatic actuator 66 causes ball joint 46 to be simultaneously locked by lever mechanism 70 as previously described.

Located within distal ball joint 48 is bearing ball 78 constrained to run simultaneously in two raceways 82 and 84. Raceway 82 is formed into ball 49 while raceway 84 is formed on the inside face of cap 72 and is substantially symmetrical about the cylindrical axis of cap 72. Raceway 84 is interrupted by dowel pin 83 placed through raceway 84 in a direction parallel to the cylindrical axis of cap 72. When ball 49 is rotated about the cylindrical axis of cap 72, bearing ball 78 is caused to rotate about that cylindrical axis inside raceway 84 until making contact with dowel pin 83 at which point further rotation of ball 49 with respect to cap 72 in that direction is prevented. This action prevents ball 49 from rotating more than 360 degrees with respect to cap 72 and limits damage to internal electrical wires 86 which pass through ball 49 and into switch housing 50 to conduct control signals from surgical retractor 10 to control box 36.

Figure 3:
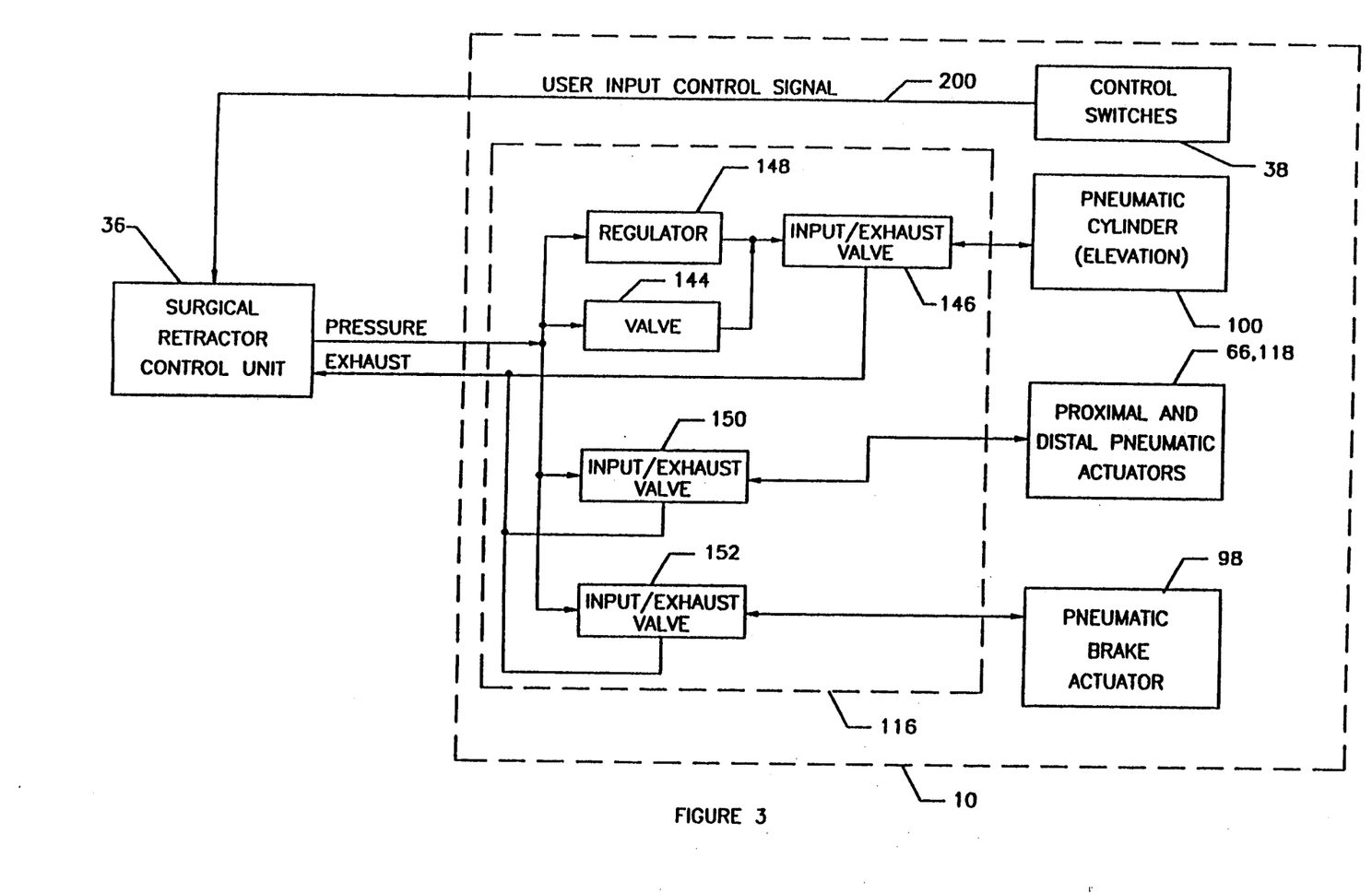
FIG. 3 is a block diagram of the control system for the elevating and position regulating component of the surgical retractor system of FIG. 1.

A control circuit for the surgical retraction system is shown in FIG. 3. As previously described, control unit 36 provides pressurized gas to and receives exhaust gas from surgical retractor 10 in response to signals on signal line 200 generated by switches 38 of surgical retractor 10. Pressurized gas is supplied by control unit 36 to pneumatic control means 116 which is now functionally described.

When activated by an electrical signal on signal line 200 from an appropriate switch 38, pneumatic control means 116 allows high pressure gas to pass through input/exhaust valve 146 to pneumatic cylinder 100 of elevating member 12. Under the force of the pressurized gas the rod of pneumatic cylinder 100 retracts inside pneumatic cylinder 100 and moves elevating member 12, distal member 14, switch housing 50 and any surgical retractor or instrument attached to switch housing 50 upwards with respect to block 24. To move the elevating member 12 in the opposite direction, input/exhaust valve 146 of pneumatic control means 116 is opened and the high pressure gas in pneumatic cylinder 100 is exhausted back to control unit 36. Pneumatic control means 116 also has input/exhaust valve 150 which allows pressurized gas to pass to and from both distal pneumatic actuator 66 and proximal pneumatic actuator 118 to lock and unlock ball joints 46 and 44 respectively. Similarly, pneumatic control means 116 has input/exhaust valve 152 to lock and unlock pneumatic brake actuator 98 to resist vertical motion of elevating member 12 with respect to block 24.

In the preferred embodiment it is possible for an operator to select either a NORMAL elevating force or a HIGH elevating force by selecting the appropriate switch 38 on switch housing 50. In NORMAL mode, pneumatic control means 116 regulates pressurized gas to a lower pressure by passing it through regulator 148. In HIGH force mode the pressurized gas bypasses regulator 148 and passes through valve 144 to pneumatic cylinder 100. The elevating force applied in NORMAL and HIGH force mode by elevating member 12 can be pre-determined and pre-set by knowing the input value of the pressurized gas supplied to pneumatic cylinder 100 and the plunger surface area of pneumatic cylinder 100.

OPERATION BY SURGICAL STAFF

Before using surgical retractor 10 in a surgical procedure, a user must choose and sterilize appropriate surgical instruments and assure sterility of surgical retractor 10. The preferred method for providing sterility assurance of surgical retractor 10 is to drape the apparatus with a sterile cover.

The patient is first positioned on the operating room table in a normal position for the surgical procedure to be performed, and anesthetized in accordance with standard medical procedures.

Surgical retractor 10 is attached at a suitable place on the operating room table by first loosening knurled knob 26, which moves apart upper jaw 22 from fixed lower jaw 20. This allows the operating room table accessory rail to be inserted between jaws 20 and 22. Knurled knob 26 is then tightened to force movable upper jaw 22 towards fixed lower jaw 20, thereby clamping the operating room table rail between jaws 20 and 22 to rigidly fix surgical retractor 10 to the operating room table. A sterile surgical drape is then placed over surgical retractor 10 to provide a sterile barrier between the apparatus and patient.

Cable 30 of surgical retractor 10 is attached to control box 36, which may be located away from the operating room table. Electrical power cord 42 and pressurized gas supply hose 40 are connected to control box 36 to provide appropriate electrical and pneumatic power for surgical retractor 10.

The operating surgeon selects an appropriate surgical instrument, such as a retractor blade, and connects it to surgical retractor 10 at connector 18 of switch housing 50.

In using surgical retractor 10, the operating surgeon may desire to change the position of the surgical instrument or surgical retractor 10. To do this, the operating surgeon presses one of the switches 38 on switch housing 50, which sends a control signal to control box 36 and causes control box 36 to activate appropriate valves in control box 36 and pneumatic means 116 responsively. With pneumatic means 116 activated, the high pressure gas supplied to the locking means of the ball joints is exhausted and the ball joints are released to move freely. The operating surgeon may now re-position the surgical instrument and the unlocked ball joints. When a new desired position is reached, the operating surgeon releases the switch, which deactivates the appropriate valves, causing the locking mechanisms to be re-pressurized locking the ball joints, thereby locking surgical retractor 10 in a new orientation.

Another method of changing the position of the surgical instrument or surgical retractor 10 involves elevating surgical retractor 10 with respect to block 24. The elevating mechanism of surgical retractor 10 can be operated in two modes, NORMAL and HIGH force. During use, the operating surgeon would initially attempt to re-position surgical retractor 10 in NORMAL mode as previously described. If the elevating force is insufficient to overcome external forces on surgical retractor 10 and move the surgical instrument vertically to a new desired position then the operating surgeon may choose to elevate in HIGH force mode.

To use the elevating means and to select the mode of operation, the operating surgeon presses the appropriate switch on switch housing 50, which sends a control signal to control box 36. This control signal activates the appropriate valves in control box 36 and pneumatic control means 116 which passes pressurized gas to pneumatic cylinder 100. With pneumatic control means 116 activated, gas is exhausted from pneumatic brake actuator 98 causing elevating member 12 to unlock and be moved upwards by the pneumatic cylinder 100. The operating surgeon may now reposition the surgical instrument. When a new desired position is reached, the operating surgeon releases the switch, which deactivates the appropriate valves, repressurizing pneumatic brake actuator 98 thereby locking the surgical retractor 10 in the new desired position. In a similar manner, the elevating mechanism can be moved in the opposite direction by sending a control signal to activate the appropriate valves to exhaust the pressurized gas in pneumatic cylinder 100.

When the surgical procedure is complete, the surgical instrument is removed from surgical retractor 10, cable 30 is unplugged from control box 36, and knurled knob 26 is loosened to allow jaws 20 and 22 to separate and release their grip on the operating room table rail. Electrical plug 42 and pneumatic hose 40 are then disconnected from control box 36, and surgical retractor 10 and control box 36 are then removed to storage.

Many alterations and adaptations may be made to the preferred embodiment described herein. Accordingly, the invention is to be limited only by reference to appended claims. For example, although the preferred embodiment herein described consists of two positioning members, more or fewer positioning members could be used for increased functional capability. The size of these members can also be changed to better suit the requirements of the surgical procedure in which the invention is being used. Moreover, each member may include selectably positionable joints rather than simultaneously locking or unlocking all of the ball joints of surgical retractor 10. This can be readily accomplished by selectively activating the actuation means which lock and unlock the ball joints.

Furthermore, the positioning apparatus could also be equipped with a variety of retractors or instrument holders to grip other surgical instrumentation, such as arthroscopy cameras, suction catheters, light sources, and other tools or apparatus which must be positioned near the surgical site; switch 38 herein described in the preferred embodiment could be replaced with a number of different switching mechanisms, including footswitches, voice control devices, or remote control pendants; and the tissue pressure sensing and regulating component described in the preferred embodiment could be utilized with many other retractor supporting means.

Another alternative to this preferred embodiment would be to enable a user to manually regulate the pressure of the gas supplied to pneumatic cylinder 100, thereby allowing for manual control of the elevating force of elevating means 56. Another possibility to this preferred embodiment would be an automated means for regulating the pressure of the gas supplied to cylinder 100 in response to an input signal from the user.

We claim:

1. A powered surgical retractor, comprising:
    a support member adapted for attachment to a rail member of an operating table;
    a first positioning member mounted to the support member;
    a second positioning member adjustably attached at one end to the first positioning member, the other end of the second positioning member being adapted to hold a surgical retractor; a surgical retractor held by the other end of the second positioning member; and
    fluid-driven means for applying a fluid-driven force between the support member and the first positioning member for moving the first positioning member and attached second positioning member and the retractor relative to the support member.

2. The retractor of claim 1 further including a releasable brake member operable for fixing the position of the first positioning member relative to the support member.

3. The retractor of claim 1 wherein the brake member is operated by a fluid-driven member, the retractor including valve means operable by switches for applying pressurized fluid to the fluid driven means and to the brake member and for exhausting pressurized fluid from the fluid driven means and from the brake mechanism.

4. The retractor of claim 3 further including a switch carrying member mounted to the second positioning member, the switch carrying member carrying switches for operating the valve means.

5. The apparatus of claim 1 wherein the support member includes:
    a clamp member for clamping the support member to the rail member; and
    a carriage mounted to the clamp member for movement relative thereto, the carriage carrying the first positioning member.

6. The apparatus of claim 5 further comprising a brake mounted to the clamp member and selectively operable for engaging the carriage to prevent movement of the carriage relative to the clamp member.

7. The apparatus of claim 5 wherein the fluid-driven means includes a fluid-driven actuator connected between the carriage and the clamp member and operable for applying the fluid-driven fluid to move the carriage relative to the clamp member.

8. The apparatus of claim 7 wherein the fluid-driven means includes a regulator for varying the level of the fluid-driven force applied by the fluid-driven actuator for moving the carriage relative to the clamp member.

9. The apparatus of claim 1 further comprising regulation means for varying the level of the fluid-driven force applied by the fluid-driven means.

10. Apparatus for surgical retraction, comprising:
   a clamp adaptable for clamping to the rail of an operating table, the clamp including a body;
   a carriage mounted to the body of the clamp for translational motion relative to the body;
   an elongated positioning member having one end joined to the carriage for rotation about the joined end, another end of the positioning member being connectable to a surgical retractor; and
   an elevator connected to the clamp body and including drive means for driving the translational motion of the carriage thereby to change the elevation of the carriage and joined positioning member.

11. The apparatus of claim 10 further comprising a brake mounted to the clamp body and operable by pressurized fluid for preventing motion of the carriage relative to the clamp body.

12. The apparatus of claim 10 wherein the elevator includes an actuator having an extendable and retractable length, the actuator being connected between the clamp body and the carriage and configured for receiving and exhausting pressurized fluid applied thereto for extending and retracting the actuator length.

13. The apparatus of claim 12 further comprising regulation means for varying the pressure level of the fluid applied to the actuator.

14. A method of using a surgical retraction apparatus, comprising the steps of:
   connecting a surgical retractor to a first end of an elongated positioning member;
   connecting the positioning member to a carriage member;
   providing a stationary support member;
   mounting the carriage member to the support member for movement relative to the support member; and
   connecting between the carriage member and the support member an actuator having a movable part, so that movement of the actuator part moves the carriage and connected positioning member thereby to change the position of the surgical retractor.

15. The method of claim 14 including the step of directing to and from the actuator pressurized fluid for moving the movable part of the actuator.

16. The method of claim 15 including the step of providing on the positioning member a switch for controlling the flow of pressurized fluid to and from the actuator.

17. The method of claim 14 including the step of mounting to the support member a brake for releasably locking together the carriage member and the support member.

* * * * *